United States Patent [19]
Kohno et al.

[11] Patent Number: 5,058,587
[45] Date of Patent: Oct. 22, 1991

[54] PROBE FOR OPTICAL SENSOR

[75] Inventors: Hiromasa Kohno; Masahiro Nudeshima, both of Fuji, Japan

[73] Assignee: Terumo Kabushiki Kaisha, Tokyo, Japan

[21] Appl. No.: 396,901

[22] Filed: Aug. 22, 1989

[30] Foreign Application Priority Data

Aug. 23, 1988 [JP] Japan .................. 63-207360

[51] Int. Cl.⁵ .................................. A61B 5/00
[52] U.S. Cl. .................................. 128/633
[58] Field of Search .......... 250/573, 574, 576; 604/4; 128/632, 633, 635

[56] References Cited

U.S. PATENT DOCUMENTS

| | | | |
|---|---|---|---|
| 3,068,742 | 12/1962 | Hicks, Jr. et al. | 128/634 |
| 4,166,961 | 9/1979 | Dam et al. | 250/573 |
| 4,201,471 | 5/1980 | Pitt et al. | 250/574 |
| 4,253,448 | 3/1981 | Terada | 128/4 |
| 4,444,498 | 4/1984 | Heinemann | 356/246 |
| 4,561,779 | 12/1985 | Nagamune et al. | 250/573 |
| 4,710,025 | 12/1987 | Wyatt et al. | 250/574 |
| 4,740,709 | 4/1988 | Leighton et al. | 250/573 |
| 4,917,491 | 4/1990 | Ring et al. | 356/300 |

FOREIGN PATENT DOCUMENTS

| | | |
|---|---|---|
| 0013611 | 7/1980 | European Pat. Off. . |
| 0240742 | 6/1987 | European Pat. Off. . |
| 0259951 | 3/1988 | European Pat. Off. . |
| 1803863 | 7/1969 | Fed. Rep. of Germany . |
| 2263890 | 7/1973 | Fed. Rep. of Germany . |
| 2215984 | 8/1974 | Fed. Rep. of Germany . |
| 2508637 | 9/1976 | Fed. Rep. of Germany . |
| 2823769 | 12/1979 | Fed. Rep. of Germany . |

*Primary Examiner*—Kyle L. Howell
*Assistant Examiner*—Kevin Pontius
*Attorney, Agent, or Firm*—Burns, Doane, Swecker & Mathis

[57] ABSTRACT

An optical sensor probe for emitting light into blood and detecting light reflected by the blood, having one end of a first light transmitting member brought into contact with blood flowing through a conduit, and capable of emitting light into the blood in the conduit by introducing the light into the first light transmitting member from the other end thereof. Part of the light emitted into the blood by the first light transmitting member and reflected by the blood is introduced into the second light transmitting member from one end of the same in contact with the blood and is transmitted to a light detecting device. The end of the second light transmitting member is disposed in a side wall of the conduit at a predetermined distance from the end of the first light transmitting member in contact with the blood.

6 Claims, 5 Drawing Sheets

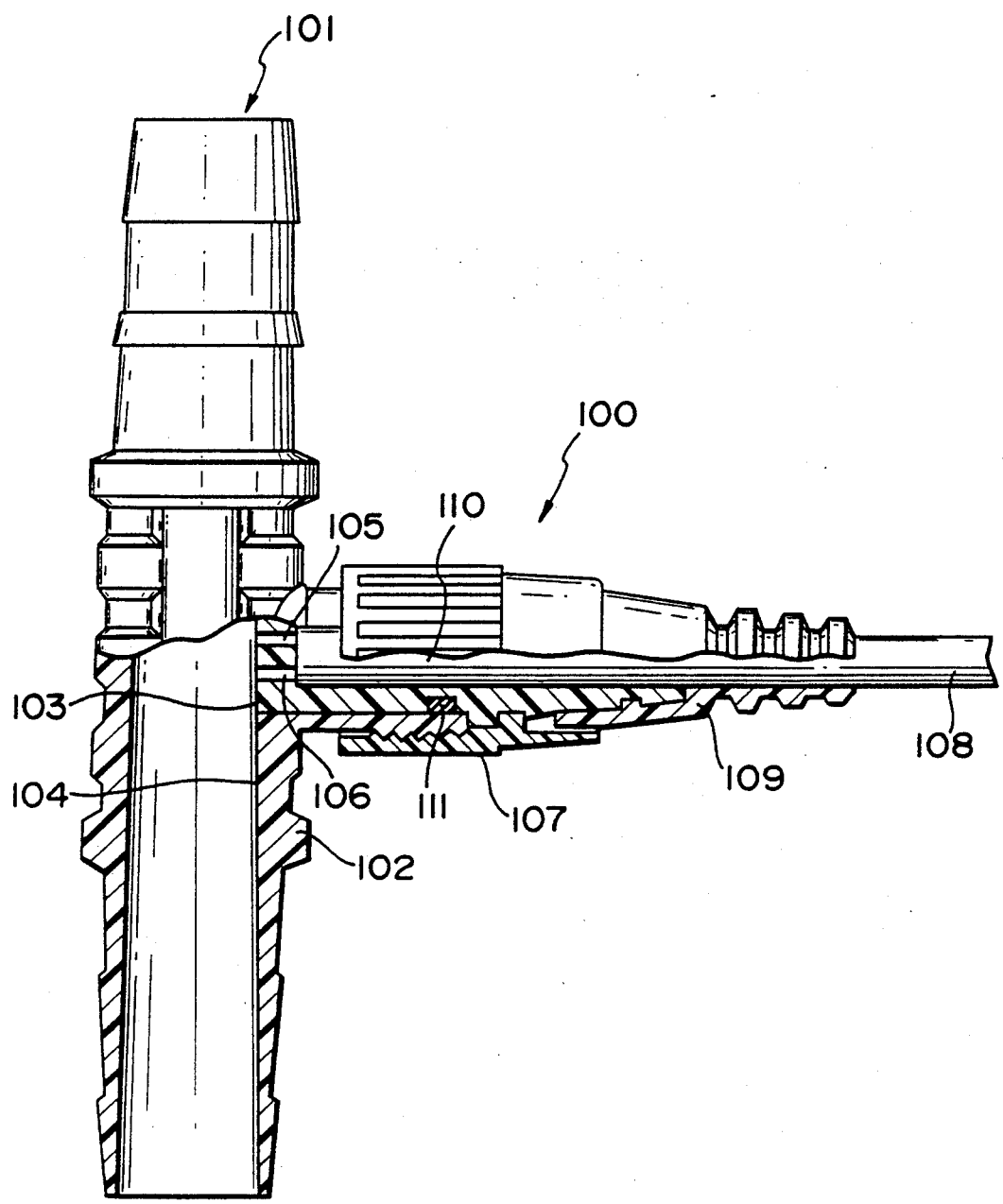
F I G. 1

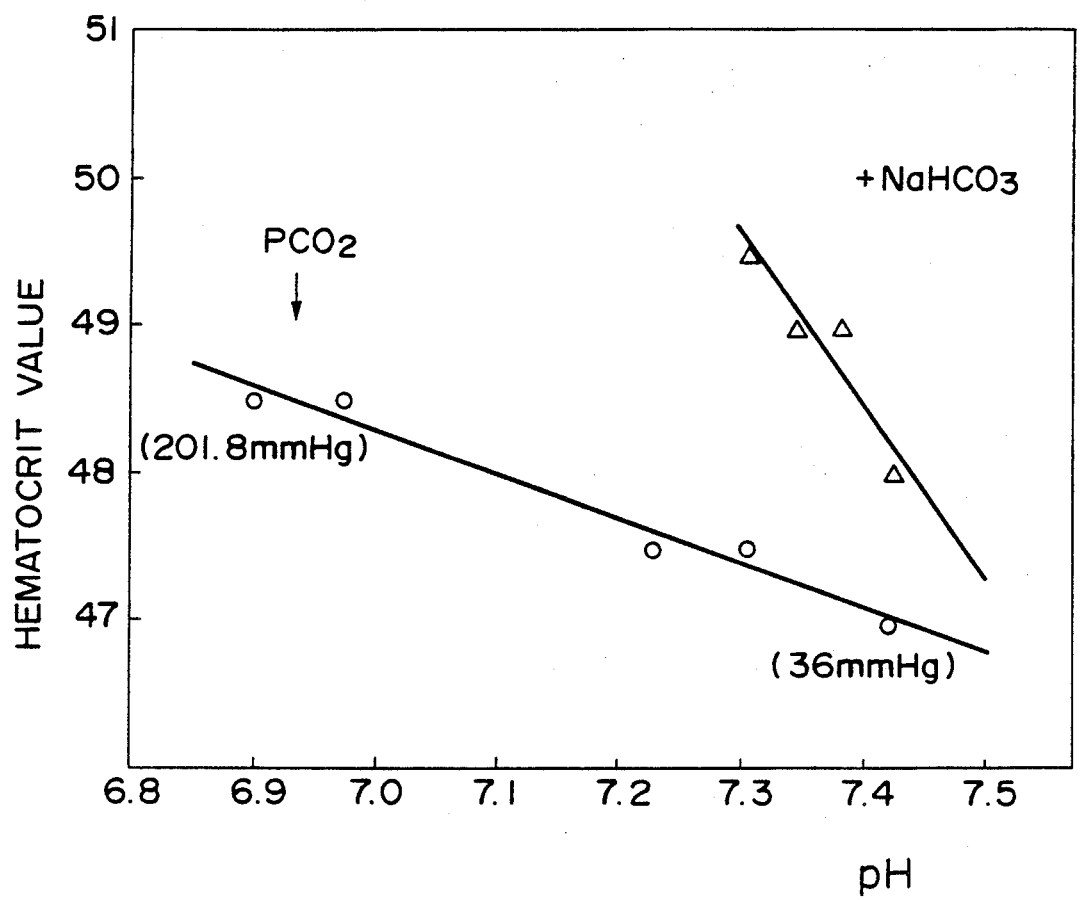
F I G. 3

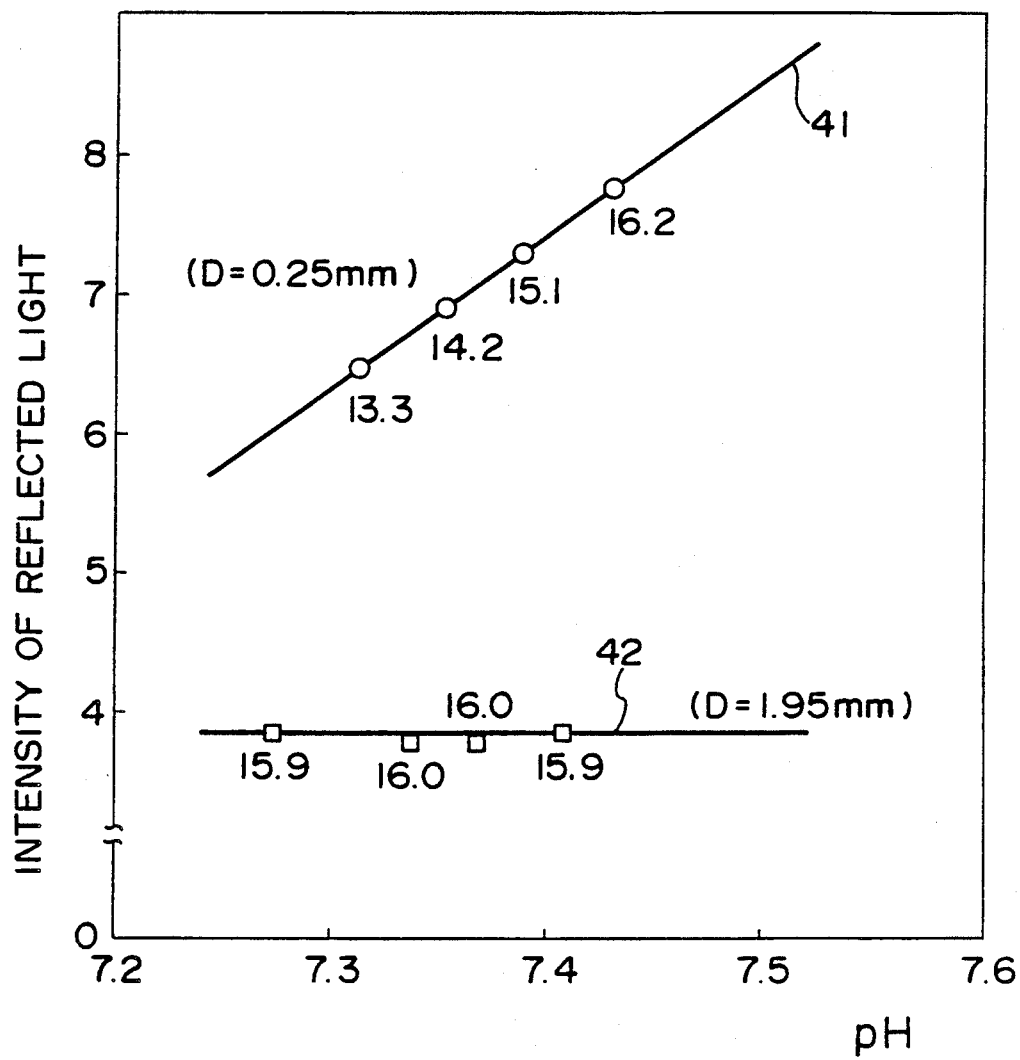
F I G. 4

PROBE FOR OPTICAL SENSOR

BACKGROUND OF THE INVENTION

1. Field of the Invention

This invention relates to a probe for an optical sensor used to measure the degree of oxygen saturation in hemoglobin and the hemoglobin concentration in blood or an organism. More particularly, the present invention relates to an optical sensor probe used by being inserted in an extracorporeal circulation circuit such as a pump-oxygenator circuit to continuously monitor the degree of oxygen saturation in hemoglobin and the hemoglobin concentration.

2. Description of the Related Art

For open heart surgery or the like, extracorporeal circulation is temporarily effected by using a pump-oxygenator instead of the heart and the lung of the organism. To know the oxygen transport rate of blood circulation and the oxygen consumption in the organism during the extracorporeal circulation, the degree of oxygen saturation in blood in arteries and veins and the hemoglobin concentration thereof are measured by periodically sampling the blood. In this system, the oxygen saturation cannot be continuously examined. There is therefore a risk of a delay of the desired treatment for an abrupt change in the physical state of the subject or patient. A method for preventing such a risk is well known in which the blood of the subject is irradiated with light having a particular wavelength and the degree of oxygen saturation is obtained from the intensity of the reflected light or transmission light. Measurement of hemoglobin concentration has also been studied but no method for measuring this factor with accuracy has been established.

Conventional detectors for detecting the intensity of light reflected in blood are designed to be immersed in blood to detect the intensity of reflected light and therefore entail the following problems. During immersion in blood for a long time, characteristics of circuit component parts are changed under the influence of the temperature of the blood and so on, and the value of the intensity of reflected light detected is thereby changed, resulting in difficulty in measuring the hemoglobin concentration and other quantities with accuracy. There is also a risk of leakage of electricity since electric circuit parts are immersed in blood.

Moreover, in the case of monitoring based on continuous measurement of the hemoglobin concentration, the intensity of reflected light cannot be measured with stability and accuracy due to the influence of the size and shape of blood cells although the intensity of reflected light is correlative to the hemoglobin concentration.

SUMMARY OF THE INVENTION

In view of these circumstances, an object of the present invention is to provide an optical sensor probe which makes it possible to continuously measure the intensity of light reflected in blood with safety and with accuracy.

Another object of the present invention is to provide an optical sensor probe designed to completely insulate light transmitting members electrically from an electric circuit section by using optical fibers as the light transmitting members in order to eliminate the risk of leakage of electricity.

A still another object of the present invention is to provide an optical sensor free from any influence of the temperature of blood on temperature characteristics of electronic parts including an operational amplifier.

A further object of the present invention is to provide an optical sensor probe designed to obtain the intensity of reflected light substantially irrespective of properties of blood cells including the size of red blood cells by increasing the distance between a light emitting portion and a light receiving portion constituted by end surfaces of optical fibers while maintaining suitable performance of detecting the intensity of reflected light.

A still further object of the present invention is to provide an optical sensor probe which makes it possible to continuously measure the intensity of reflected light while maintaining electrical insulation for safety and to improve the accuracy with which the degree of oxygen saturation and the hemoglobin concentration are calculated on the basis of measured light intensities.

To achieve these objects, in accordance with the present invention, there is provided an optical sensor probe for emitting light into blood and detecting light reflected by the blood, the optical sensor probe comprising:

a conduit through which the blood flows; a first light transmitting member having its one end brought into contact with the blood in said conduit, said first light transmitting member being supplied at its other end with light and emitting the light into the blood; a second light transmitting member having its one end disposed in a side wall of said conduit at a predetermined distance from said end of said first light transmitting member in contact with the blood, said second light transmitting member receiving at its said end reflected part of the light emitted into the blood by said first light transmitting member, said second light transmitting member transmitting the received reflected light to a light detecting device.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a diagram of the construction of an optical sensor probe which represents an embodiment of the present invention;

FIG. 3 is a diagram of the hematocrit value with respect to pH changed by controlling the partial pressure and concentration of carbon dioxide in blood;

FIG. 4 is a diagram of the intensity of reflected light with respect to pH in a case where the distance between the light emitting and light receiving optical fibers is 0.25 mm as well as in a case where this distance is 1.95 mm.

DESCRIPTION OF THE PREFERRED EMBODIMENT

A preferred embodiment of the present invention will be described below with reference to the accompanying drawings.

Figure 2:
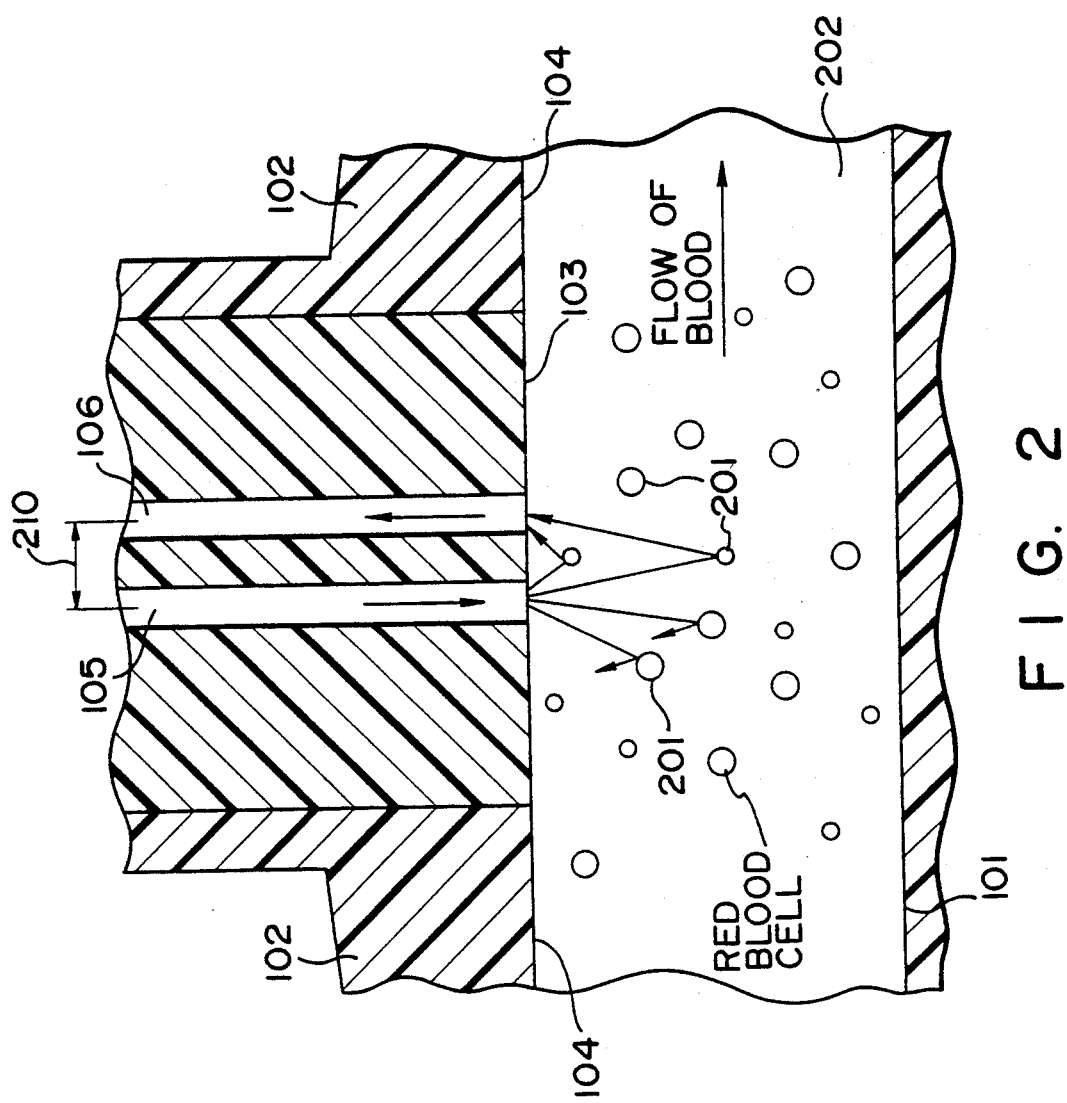
FIG. 2 is a schematic diagram of propagation of light emitted, reflected by red blood cells and introduced into a light receiving portion.

Description for Probe (FIGS. 1 and 2)

FIG. 1 shows in section the configuration of an optical sensor probe which represents an embodiment of the present invention with a portion thereof cut away for illustration, and FIG. 2 is a schematic diagram of propagation of light emitted from a light emitting portion, reflected by red blood cells and introduced into a light receiving portion.

Referring to FIG. 1, an optical sensor probe 100 is fixed by a connector 102 to a conduit 101 which constitutes an extracorporeal circulation circuit and which is filled with blood flowing therethrough. An end surface 103 of the probe 100 is worked so as to be flat and flush with an inner wall surface 104 of the connector 102 in order to prevent the flow of blood from being disturbed. The optical sensor probe 100 is basically formed of four parts: a probe body 110 in which two optical PMMA (polymethylmethacrylate) fibers 105 and 106 are accommodated and fixed; a fixing nut 107 for fixing the probe body 110 to the connector 102; a soft polyvinyl chloride cap 109 for preventing a polyvinyl chloride tube 108, for protection of the optical fibers 105 and 106, from being bent with an extremely large curvature at the position of connection to the optical sensor probe 100; and an O-ring 111 for preventing any leak of blood. Quartz fibers may be used instead of the PMMA fibers.

The two optical fibers 105 and 106 are fixed in the probe 100 of this embodiment. One (105) of these optical fibers constitutes a light emitting portion through which light transmitted from a light source such as an LED is introduced into the conduit 101 to irradiate blood, and the other optical fiber 106 is used to transmit part of light introduced into the blood through the optical fiber 105 and reflected by red blood cells in the blood to a light detecting element such as a photodiode capable of detecting the intensity of light.

Referring then to FIG. 2, light having a particular wavelength is emitted into blood 202 from the light emitting portion constituted by the end surface of the optical fiber 105 in contact with the blood in the conduit 101. Part of light reflected by red blood cells 201 is introduced into the light receiving portion constituted by the optical fiber 106. The introduced part of the reflected light is transmitted to the unillustrated light detecting element through the optical fiber 106, thereby measuring the intensity of the light reflected in the blood.

The intensity of this reflected light is changed if the distance 210 between the optical fibers 105 and 106 is changed. This effect is thought to be based on dependence of the intensity of the reflected light upon the path through which light emitted from the optical fiber 105 travels in the blood 202 and reaches the light receiving portion while repeating scattering, as explained below briefly. If the distance 210 (between the centers of the optical fibers 105 and 106) is small, the proportion of scattered light from the vicinity of the end contact surfaces of the fibers 105 and 106 in the detected reflected light is large. As the distance 210 is increased, the proportion of scattered light from red blood cells 201 remote from the end contact surfaces increases.

Consequently, if the distance 210 between the light emitting optical fiber 105 and the light receiving optical fiber 106 is increased, the influence of disturbance of the blood flow in the vicinity of the connector inner wall 104 and the influence of hematocrit variation upon the intensity of the reflected light are small. An increase in the distance 210 also results in an improvement in the diffusion of light. It is thereby possible to receive uniform reflected light by limiting the influence of the size of the red blood cells and other factors.

Explanation of Results of Measurement (FIGS. 3 and 4)

FIG. 3 shows changes in the hematocrit value with respect to the blood pH changed by controlling the partial pressure of carbon dioxide $PCO_2$ and the $NaHCO_3^-$ concentration in the blood in mmHg and mM unit, respectively. FIG. 4 shows the intensity of reflected light having a wavelength of 800 nm with respect to pH values in a case where the distance between the irradiating and light receiving optical fibers was 0.25 mm or as well as in a case where the distance between these fibers was 1.95 mm.

Referring to FIG. 3, the hematocrit value changed in proportion to the blood PH value with respect to each value of the carbon dioxide $PCO_2$ and the $NaHCO_3^-$ concentration. This effect is thought to be mainly based on expansion or shrinkage of red blood cells due to changes in the osmotic pressure.

In FIG. 4, the intensity of reflection light with respect to pH when the distance D (210) was 0.25 mm is indicated at 41, and the intensity of reflection light with respect to pH when the distance D (210) was 1.95 mm is indicated at 42. As shown in FIG. 4, when the distance D between the pair of light emitting and light receiving optical fibers was smaller than 1.5 mm, the influence of pH was large or, when the distance D was increased, the influence of pH was reduced. However, when the distance D was 3.0 mm or more, the sensitivity was reduced. Values shown with symbols in FIG. 4 were calculated by a later-mentioned formula for calculating the hemoglobin concentration. In this experiment, each of the two optical fibers 105 and 106 was an optical PMMA plastic fiber having a diameter of 0.25 mm when the distance D was 0.25 mm or a diameter of 0.75 mm when the distance D was 1.95 mm.

As can be understood from these results, although the size of red blood cells varies in different organisms, the light intensity reflected by red blood cells can be measured without depending upon the size of the red blood cells if the distance D is set to a suitable value.

In this experiment, it was suitable to set the distance D to 1.95 mm, but other values of the distance D within the range of 1.5 mm to 3.0 mm were to be considered because the optimum value of the distance D depends upon the diameter of the optical fibers employed and other factors.

The hemoglobin concentration [Hb] with respect to incident light having a wavelength of 800 nm was calculated from the reflection light intensity E by using the following formula:

$$[Hb] = aE^2 + bE + C$$

The coefficients a, b and c in this formula depend upon the characteristics of the optical sensor. More specifically, if the distance D between the optical fibers is 0.25 mm, $$[Hb] = 0.084 \ E^2 + 0.921 \ E + 3.72$$

In the case where the distance D between the optical fibers is 1.95 mm, $$[Hb] = 0.929 \ E^2 - 2.46 \ E + 24.8$$

In the above-described embodiment, the light emitting portion for introducing light into blood and the light receiving portion for receiving light reflected in blood are constituted by end portions of the optical fibers. However, the present invention is not limited to this arrangement and can of course be arranged in such a manner that a light emitting device such as a light emitting diode (LED) constitutes the light emitting portion to be brought into contact with blood while a light receiving device such as a photosensor constitutes the light receiving portion to be brought into contact with blood. In this case, needless to say, the portions including the LED and the photosensor to be brought into contact with blood are electrically insulated.

Figure 5:
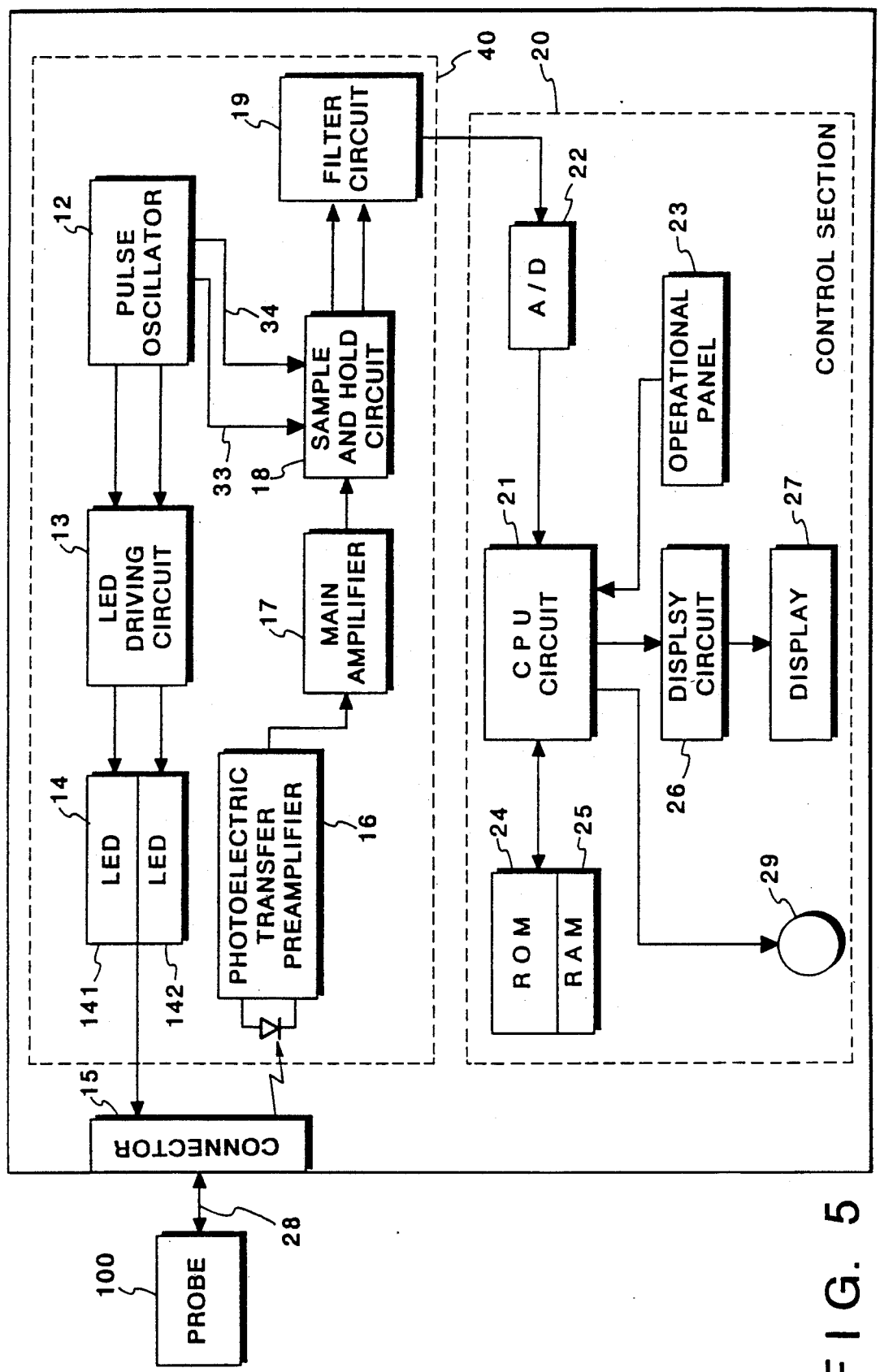
FIG. 5 is a schematic block diagram of the construction of an oxygen saturation measuring apparatus in accordance with the embodiment.

FIG. 5 shows a schematic block diagram of the construction of an apparatus for measuring the oxygen saturation by using the optical sensor probe 100 of the above-described embodiment.

Referring to FIG. 5, the probe 100 is used by being inserted in an extracorporeal circulation circuit such as a pump-oxygenator circuit to measure the intensity of light reflected in blood. A pulse oscillator 12 outputs drive timing signals for driving an LED assembly 14 (LEDs 141 and 142) to an LED driving circuit 13, and also outputs timing signals for sampling the reflected light intensity with respect to different wavelengths to a sample and hold circuit 18. The LED driving circuit 13 drives one of the LEDs 141 and 142 of the LED assembly 14 to effect emission of light. The LED assembly 14 is capable of outputting light having a wavelength of 660 nm or light having a wavelength of 800 nm. In this embodiment, two light emitting diodes LED 141 (wavelength: 660 nm) and LED 142 (wavelength: 800 nm) constitute the LED assembly 14. Lights having different wavelengths emitted from respective LEDs are introduced into one optical fiber through an optical coupler and is supplied to the optical fiber 105 of the probe 100.

The LED assembly may be replaced by one LED if the wavelength of light output from this LED can be changed between 660 nm and 800 nm by, for example, changing the driving voltage.

A connector 15 is provided for connection between the probe 100 and the body of the apparatus. The probe 100 and the apparatus body are connected to the cable 108 in which the optical fibers 105 and 106 are accommodated. In a section 16, a photoelectric transfer device and a preamplifier are integrally disposed. The section 16 is supplied with reflected lights transmittee through the optical fiber 106 of the probe 100 and outputs an electric signal representing the intensities of the supplied lights. A main amplifier 17 further amplifies the electric signal supplied from the photoelectric transfer section 16. The sample and hold circuit 18 is supplied with the timing signals from the pulse oscillator 12 and samples and holds the analog signal supplied from the main amplifier section 17 in synchronization with the timing signals.

Lights of the respective wavelengths emitted from the LED assembly 14 are controlled by using the timing signals supplied from the pulse oscillator 12 so as to avoid any overlap of these lights with respect to time. The intensities of reflected lights of the respective wavelengths are held by the sample and hold circuit 18 independently of each other. Noise components of a signal supplied from the sample and hold circuit 18 are filtered off by a filter circuit 19 and the signal is thereafter supplied to a control section 20.

In the control section, the analog signal supplied from the filter circuit 19 is converted into a digital signal by an A/D converter 22 and is supplied to a CPU circuit 21.

The CPU circuit 21 that includes a microprocessor and so on performs control operations in accordance with control programs and various items of data stored in a ROM 24. A RAM 25 is used as a working area for the CPU circuit, and various items of data are temporarily stored in the RAM 25. An operational panel 23 through which the apparatus is operated by the operator, and a command to start measurement and various kinds of instructions can be input by using the operational panel 23. A display 27 is driven by a display circuit 16 to display messages to the operator, results of measurement and so on. An external output terminal 29 is provided to output information including measurement data to an external unit such as a printer connected to the apparatus.

Next, a measurement process conducted by this oxygen saturation measuring apparatus will be described below briefly.

As described above, a plurality of values representing the intensities of lights of the wavelengths of 660 nm and 800 nm reflected in blood are obtained and the averages of these values are calculated. This step is necessary for reducing the influence of errors in information on the respective reflected light intensities. The average values of the reflected light intensities are normalized by the following calculation. The intensity of light reflected by a white board having a constant reflectance is calculated with respect to each wavelength, and the intensities thereby obtained are set as W660 and W800. Let the above average reflected light intensities be R660 (the average reflected light intensity with respect to wavelength of 660 nm) and R800 (the average reflected light intensity with respect to wavelength of 800 nm), respectively. Normalized values ($N_1$, $N_2$) are then expressed by the following equations:

$$N_1 = R660/W660$$

$$N_2 = R800/W800$$

From the thus-normalized average reflected light intensities, the degree of oxygen saturation is calculated by using the following equation:

$$SO_2 = a_3(N_1/N_2)^3 + a_2(N_1/N_2)^2 + a_1(N_1/N_2) + a_0 \quad (3)$$

where $a_0$, $a_1$, $a_2$ and $a_3$ are constants which depend upon the characteristics of the optical sensor probe 100 and the animal species. For example, twenty values (measured in five seconds) are averaged with respect to each wavelength, the averaged values are calibrated, and the degree of oxygen saturation is calculated from these values. For example, the above constants are as follows: $a_0 = 104.0$, $a_1 = -11.08$, $a_2 = -26.39$, and $a_3 = 6.406$.

As many apparently widely different embodiments of the present invention can be made without departing from the spirit and scope thereof, it is to be understood that the invention is not limited to the specific embodiments thereof except as defined in the appended claims.

What is claimed is:

1. An optical sensor probe for emitting light into blood and for transmitting reflected light thereby obtained to an optical sensor, said optical sensor probe comprising:

a conduit through which blood flows;

a first optical fiber having its one end adapted to be in contact with blood and connected to a side wall of said conduit so as to be flush with the inner surface of the side wall in said conduit, said first optical fiber having means for being supplied at its other end with light and emitting the light into the blood from said one end;

a second optical fiber having its one end disposed so as to be flush with the inner surface of the side wall of said conduit at a predetermined distance from said one end of said first optical fiber in the direction in which the blood flows through said conduit, said second optical fiber receiving at its said one end reflected part of the light emitted into the blood by said first optical fiber, and transmitting the received reflected light to said optical sensor;

a cable accommodating said first and second optical fibers; and connection means for connecting said cable to a side surface of said conduit.

2. An optical sensor probe according to claim 1, wherein said predetermined distance is within a range of 1.5 mm to 3.0 mm.

3. An optical sensor probe according to claim 1, wherein said connection means includes an O-ring for preventing leakage of the blood, and a limiting member for limiting bending of the cable.

4. An optical sensor probe for emitting light into blood and for transmitting reflected light thereby obtained to an optical sensor, said optical sensor probe comprising:

a conduit through which blood flows;

a first optical fiber having a light emitting portion through which light transmitted from a light source is introduced into said conduit, said light emitting portion being adapted to be in contact with blood and connected so as to be flush with an inner surface of a side wall in said conduit;

a second optical fiber having a light receiving portion to which is introduced part of light reflected by said blood, said light receiving portion being adapted to be in contact with blood and connected so as to be flush with the inner surface of the side wall of said conduit at a predetermined distance from said light emitting portion of said first optical fiber in the direction in which the blood flows through said conduit, said second optical fiber also having means for transmitting the light received by said light receiving portion to said optical sensor;

a cable accommodating said first and second optical fibers;

connection means for connecting said cable to said conduit; and a limiting member for limiting said cable from being bent at the connecting point of said cable and said conduit.

5. An optical sensor probe according to claim 4, wherein said predetermined distance is within a range of 1.5 mm to 3.0 mm.

6. An optical sensor probe according to claim 4, wherein said connection means includes an O-ring for preventing leakage of the blood.

* * * * *